Figure 1:
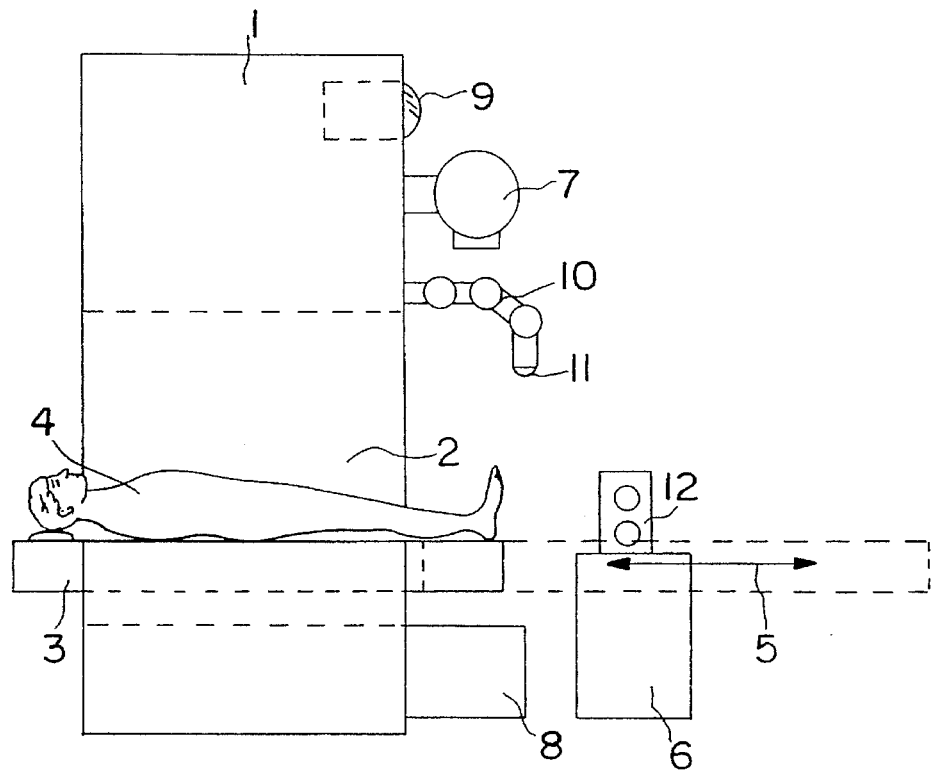

United States Patent [19]

Grönemeyer et al.

[11] Patent Number: 5,533,082
[45] Date of Patent: Jul. 2, 1996

[54] COMPUTER TOMOGRAPH

[76] Inventors: Dietrich H. W. Grönemeyer; Rainer M. M. Seibel, both of Schulstr. 10, D-4330 Muehlheim/Ruhr, Germany

[21] Appl. No.: 211,470
[22] PCT Filed: Oct. 14, 1992
[86] PCT No.: PCT/EP92/02362
§ 371 Date: Mar. 30, 1994
§ 102(e) Date: Mar. 30, 1994
[87] PCT Pub. No.: WO93/14697
PCT Pub. Date: Aug. 5, 1993

[30] Foreign Application Priority Data

Jan. 28, 1992 [DE] Germany ............. 42 02 302.5

[51] Int. Cl.⁶ .................................. A61B 17/22
[52] U.S. Cl. ................. 378/20; 378/64; 378/65; 378/206
[58] Field of Search ................... 378/4, 62, 64, 378/65, 68, 69, 98, 98.2, 98.3, 98.5, 21, 8, 20, 205, 206, 177

[56] References Cited

U.S. PATENT DOCUMENTS

| 5,077,769 | 12/1991 | Franciose ................. 378/98.2 |
| 5,080,100 | 1/1992 | Trotel ........................ 378/206 |
| 5,231,651 | 7/1993 | Ozaki et al. ................. 378/4 |
| 5,265,610 | 11/1993 | Darrow et al. ............. 378/62 |
| 5,329,567 | 7/1994 | Ikebe ......................... 378/65 |
| 5,395,299 | 3/1995 | Herrmanne et al. ...... 378/162 |

FOREIGN PATENT DOCUMENTS

| 0077899 | 5/1983 | European Pat. Off. . |
| 0168559 | 1/1986 | European Pat. Off. . |
| 0288698 | 11/1988 | European Pat. Off. . |
| 3636678 | 5/1988 | Germany . |
| 8713524 | 3/1989 | Germany . |

*Primary Examiner*—Don Wong
*Attorney, Agent, or Firm*—Collard & Roe

[57] ABSTRACT

A computer Tomograph having a housing with an aperture (2) for the patient in which computer-controlled scanning devices are arranged to generate computer tomograms, and into which a motor-driven, and also computer-controlled, patient's couch can be inserted from the front of the housing (1). The patient's couch also acts as an operating table, such that as little information as possible is lost in the treatment of the patient between diagnosis and the action on, or treatment of, the patient. The action or treatment can thereby be as close as possible to the diagnosis both in time and place. At the front of the housing (1), there is a plurality of information displays connected to the computer, especially in the form of display screens. In front of the housing (1) there is an operation and treatment area for the patient, to which further diagnostic and/or operative and/or therapeutic auxiliaries are allocated.

10 Claims, 1 Drawing Sheet

COMPUTER TOMOGRAPH

The invention relates to a computer tomograph consisting of a housing with an aperture for receiving the patient, in which housing computer-controlled scanning units are arranged for generating computer tomograms, and into which a motor-driven and also computer-controlled patient's couch can be driven from the front side of the housing.

The computer tomographs commonly used according to the state of the art are exclusively used for diagnostic purposes. They generate sectional pictures through the body of the patient arranged in various planes of section. The customary scanning units of computer tomographs operate with X-rays or on the basis of a measurement and evaluation of the magnetic core spin resonance in the body tissue of the patient to be examined. A particularity of the computer tomographs consists in that the tomograms cannot be produced immediately but only with some time delay because the arithmetic algorithm for the evaluation of the values measured in the scan requires very extensive arithmetic operations. However, such time delay now comes to only a few seconds due to the high efficiency of modern data processing equipment.

It is disadvantageous in connection with the conventional use of computer tomographs that the diagnosis, on the one hand, and the surgical intervention or purposeful treatment of the patient, on the other hand, are separated from each other in terms of place and time, so that there is the risk that between the making of the diagnosis and the intervention on the patient, information is lost. The knowledge of such information, however, is a precondition for the success of the intervention or treatment. Special problems are caused on account of the fact that on the operating table on which the actual operation is performed, the patient assumes in most cases a completely different body position than during the diagnosis in the computer tomograph, which makes it difficult to exactly localize the organs and body parts to be treated during the planning of the operation and during the subsequent operation.

Therefore, the problem of the invention is to further develop the computer tomograph of the type specified above in that as little information as possible is lost between the diagnosis and the intervention, and that the intervention or the treatment of the patient is as close as possible to the diagnosis in terms of place and time in order to permit a superior and more exact planning or execution of the operation or treatment.

For solving said problem, the invention proposes on the basis of the computer tomograph of the type specified above that the patient's couch is at the same time designed as an operating table; that several information displays connected with the computer, particularly in the form of display screens, are arranged on the front side of the housing; and that an operation and treatment area for the patient is arranged in front of the front side of the housing, with additional diagnostic and/or operative and/or therapeutic auxiliaries being associated with said area.

The computer tomograph according to the invention makes it possible to operate on or treat the patient in some other way directly in front of the computer tomograph, i.e., directly after the diagnosis with the help of computer tomograms and without having to transfer the patient to a separate operating table. Also, special operative and/or therapeutic auxiliaries can be used for the intervention or treatment, such as, for example, a surgical laser knife, a lithotripter, or devices for the radiation therapy etc. In this connection, current information from the diagnosis just made is available in each case to the treating physician on the display screens on the front side of the housing of the computer tomograph. Furthermore, additional patient data can be blended in on the information displays, or additional pictures can be displayed there that are helpful to the physician during the treatment or intervention.

Usefully, an X-ray tube is arranged on the front side of the housing above the patient's couch, and an X-ray oicture amplifier is arranged above the patient's couch for producing an x-ray picture of the patient lying on the couch, said picture being reproducible on a display screen of the information displays. Said additional X-ray picture display makes it possible to supply the treating physician before the intervention or before the treatment once again with a current X-ray photograph of the patient lying on the patient's couch, namely with an X-ray picture extending in a different plane than the previously generated computer tomograms.

Furthermore, the X-ray tube, on the one hand, and the X-ray picture amplifier, on the other hand, are secured with adjustability on all sides on the front side of the housing of the computer tomograph. This makes it possible to produce X-ray pictures of all possible details and in all conceivable planes.

Moreover, a position indicator is arranged on the front side of the housing on an arm that is movable on all sides and computer-controlled, and which generates at least one beam of light directed at the site of intervention or treatment on the body of the patient. Said position indicator is controlled by the central computer of the overall plant and, for its control, can use information from the computer tomograms or the other patient data stored in the computer.

Usefully, the position indicator generates several beams of light, which extend crossing each other or at an angle relative to each other and indicate to the surgeon the site of intervention and, for example, the direction of the intervention.

Usefully, the light beam is a laser beam that can be used also for treating the surface of the body (laser therapy), if need be.

According to an advantageous further development, provision is made that an ultrasound display screen is associated with the operation and treatment area, of which the pictures can be displayed on a display screen of the information displays on the front side of the housing of the computer tomograph as well. Such an ultrasound display screen can supply the treating physician with additional valuable information.

Also, an endoscope can be associated with the operation and treatment area, of which the endoscopic pictures can be represented on a display screen of the information displays as well. In this way too, additional valuable information is offered to the physician for his intervention.

The movements of the patient's couch are usefully voice-controlled. It is possible in this way to carry out the required displacements or movements of the patient's couch without touching any switches or the like.

Special advantages are achieved if additional important functions of the computer tomograph and the diagnostic and/or operative and/or therapeutic auxiliaries are voice-controlled. In this way, basically the same advantages as with the voice control of the patient's couch are obtained.

Alternatively, certain functions of the computer tomograph and of the diagnostic and/or operative and/or therapeutic auxiliaries can also be controlled by body movements. This type of control of the functions saves in the individual case the actuation of switches or the like.

So that the computer tomograph can be reset for different operations or treatments, if need be, all diagnostic and/or operative and/or therapeutic auxiliaries associated with the computer tomograph are usefully structured modular.

Figure 2:
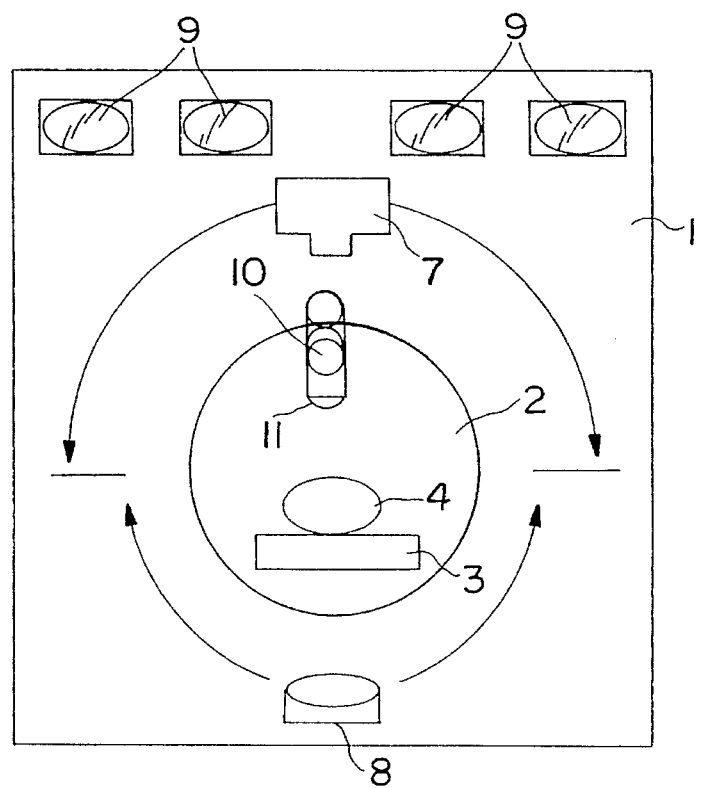

An exemplified embodiment of the invention is shown in greater detail in the following on the basis of the drawing, in which:

FIG. 1 shows a schmetaic lateral view of the tomograph according to the invention; and FIG. 2 shows a front view of the computer tomograph.

In the drawing, the housing of the computer tomograph is denoted by the reference numeral 1. The housing has an aperture 2 with a round cross section for receiving the patient, into which a patient's couch 3 can be inserted. In the drawing, the patient is denoted by the reference numeral 4. The patient's couch 3 with the patient 4 lying thereon can be driven computer-controlled into the patient-receiving aperture 2 by means of a motor drive not shown in detail, and driven out through said aperture 2 as indicated by the double arrow 5. All functions of the computer tomograph are controlled by a computer not shown in the drawing. To this extent, the computer tomograph shown in the drawing corresponds with the state of the art.

According to the invention, the patient's couch 3 is at the same designed as an operating table and, therefore, has the devices commonly used with operating tables for fixing the patient in a certain position. Furthermore, according to the invention, an operation and treatment area 4 is located in front of the patient-receiving aperture 2 of the housing 1. Operative and/or therapeutic auxiliaries are associated with said operation and treatment area; said auxiliaries are shown in the drawing in a highly simplified way and in summary denoted by the reference numeral 6.

Within the zone of the operation and treatment area, i.e., on the front side of the housing 1, an X-ray tube 7 and an X-ray picture amplifier 8 for producing an X-ray picture of the patient 4 lying on the patient's couch 3 are arranged as additional diagnostic auxiliaries. The X-ray tube 7 is designed adjustable on all sides and displaceable along a semi-circle around the aperture 3 for receiving the patient. The X-ray picture amplifier 8, too, is adjustalbe on all sides, so that different X-ray pictures of the patient 4 can be produced in cooperation with the X-ray tube 7.

Furthermore, several information displays in the form of the display screens 9 are arranged on the front side of the housing 1, on which the computer tomograms of the computer tomograph, the X-ray picture and, if need be, additional patient data important to the treating physician can be represented.

Furthermore, an arm 10 of a position indicator 11, said arm being movable on all sides and computer-controlled, is arranged on the front side of the housing 1 above the operation and treatment area. Said position indicator 11 generates one or several light beams aimed at the intervention or treatment site on the patient 4. Said light beams extent crossing each other or at an angle relative to each other and indicate to the surgeon the intervention site and, if necessary, the direction of intervention on the body of the patient 4. If need be, the light beams can be laser beams that are applicable to intervention and/or therapy purposes. Furthermore, an ultrasound display device 12 can be associated with the operation and treatment area, of which the pictures can be displayed on a display screen 9 of the information displays.

All components of the system specified above are structured modular, so that the operation and treatment area can be set up in a simple way for all types of operations and treatment.

Furthermore, all aforementioned devices are connected to the central computer of the computer tomograph. Said computer can control all movements and call up the various information functions. Said computer, which is not shown in detail in the drawing, can be controlled in the conventional way by the customary keyboards, but for controlling certain functions it can also be designed for voice control or control by body movements. The voice control is particularly advantageous for movements of the patient's couch 3 serving at the same time as the operating table, because such voice control permits the operating physician to fully concentrate on the operation and to effect any required movements of the patient's couch by voice commands.

We claim:

1. A computer tomograph apparatus including a housing having a front side with a patient receiving opening in which computer-controlled scanning devices for generating computer tomograms are arranged, and having a motor-driven, computer-controlled patient gurney designed as an operating table slidably disposed therein, the patient gurney being driven from the front side of the housing, whereby an operating and treatment station for the patient is arranged in front of the front side of the housing, the station having additional diagnostic and/or intervention aids, the front side of the housing comprising:

a plurality of information displays coupled to a computer, said displays being in the form of display screens;

an X-ray tube disposed above the patient gurney, and an X-ray picture amplifier disposed below the patient gurney for generating an X-ray photograph of the patient for display on one of said plurality of display screens; and a computer controlled arm having a position indicator arranged thereon, said arm being movable on all sides, said position indicator generating at least one light beam aimed at the site of intervention or treatment on the patient's body, the position indicator being controlled depending on information from the computer tomograms or other patient data stored in the computer.

2. The computer tomograph apparatus according to claim 1, wherein the X-ray tube (7) and the X-ray picture amplifier (8) are computer-controlled and are adjustable on all sides.

3. The computer tomograph apparatus according to claim 1, wherein the light beam of the position indicator is a laser beam.

4. The computer tomograph apparatus according to claim 1, wherein said position indicator (11) generates a plurality of light beams extending intersecting each other or at an angle relative to each other.

5. The computer tomograph apparatus according to claim 1, further comprising an ultrasound sight unit associated with the operation and treatment station, the ultrasound sight unit generating pictures being displayable on a display screen (9) of the information displays.

6. The computer tomograph apparatus according to claim 1, further comprising an endoscope associated with the operation and treatment station, the endoscope generating pictures being displayable on a display screen (9) of the information displays.

7. The computer tomograph apparatus according to claim 1, wherein the movements of the patient gurney (3) are voice-controlled.

8. The computer tomograph apparatus according to claim 1, wherein at least one function of the computer tomograph and of the diagnostic and/or intervention and/or therapy aids are voice-controlled.

9. The computer tomograph apparatus according to claim 1, wherein at least one function of the computer tomograph and/or of the intervention and/or therapy aids are controlled by body movements.

10. The computer tomograph apparatus according to claim 1, wherein the system comprises a modular construction of all assemblies of the diagnostic and/or intervention and/or therapy aids.

* * * * *